(12) United States Patent
Atis et al.

(10) Patent No.: US 8,846,018 B2
(45) Date of Patent: Sep. 30, 2014

(54) MASCARA COMPOSITIONS CONTAINING AT LEAST TWO ACRYLATE FILM FORMERS

(71) Applicant: L'Oreal, Paris (FR)

(72) Inventors: Balanda Atis, Newark, NJ (US); Hy Si Bui, Piscataway, NJ (US); Mohamed Kanji, Edison, NJ (US)

(73) Assignee: L'Oreal (FR)

( * ) Notice: Subject to any disclaimer, the term of this patent is extended or adjusted under 35 U.S.C. 154(b) by 0 days.

(21) Appl. No.: 13/632,355

(22) Filed: Oct. 1, 2012

(65) Prior Publication Data

US 2013/0028650 A1 Jan. 31, 2013

Related U.S. Application Data

(63) Continuation of application No. 12/456,505, filed on Jun. 17, 2009, now abandoned.

(60) Provisional application No. 61/132,448, filed on Jun. 18, 2008.

(51) Int. Cl.
*A61Q 1/10* (2006.01)
*A61K 8/81* (2006.01)

(52) U.S. Cl.
CPC ............... *A61Q 1/10* (2013.01); *A61K 8/8152* (2013.01)
USPC ...................................... 424/70.7

(58) Field of Classification Search
None
See application file for complete search history.

(56) References Cited

U.S. PATENT DOCUMENTS

| | | | |
|---|---|---|---|
| 4,423,031 A * | 12/1983 | Murui et al. ............... 424/63 |
| 5,441,728 A | 8/1995 | Tsaur et al. |
| 5,534,247 A * | 7/1996 | Franjac et al. ............ 424/707 |
| 5,798,426 A * | 8/1998 | Anton et al. ............ 526/318.41 |
| 6,126,929 A | 10/2000 | Mougin |
| 6,165,457 A * | 12/2000 | Midha et al. .............. 424/78.17 |
| 6,503,521 B1 * | 1/2003 | Atis et al. .................... 424/401 |
| 6,517,823 B1 * | 2/2003 | Norman et al. ........... 424/70.7 |
| 7,015,294 B2 * | 3/2006 | Dausch et al. ............. 526/319 |
| 7,094,842 B2 | 8/2006 | Lennon |
| 7,138,110 B2 | 11/2006 | Auguste et al. |
| 7,351,405 B2 | 4/2008 | De La Poterie |
| 7,351,418 B2 | 4/2008 | Collin |
| 7,651,693 B2 | 1/2010 | Merlau et al. |
| 2003/0074743 A1 | 4/2003 | Noguchi et al. |
| 2006/0134043 A1* | 6/2006 | Nakamura ................ 424/70.7 |
| 2007/0116660 A1* | 5/2007 | Kim et al. ................. 424/70.16 |
| 2007/0224140 A1 | 9/2007 | Quadir et al. |
| 2007/0246058 A1* | 10/2007 | Bodelin ..................... 132/218 |
| 2007/0272265 A1* | 11/2007 | Dupuis et al. .............. 132/203 |
| 2008/0050329 A1* | 2/2008 | De La Poterie .......... 424/70.7 |
| 2008/0107615 A1* | 5/2008 | Keene et al. ............... 424/70.7 |
| 2009/0035335 A1 | 2/2009 | Marotta et al. |

FOREIGN PATENT DOCUMENTS

EP           0466409 A1 *  1/1992

* cited by examiner

*Primary Examiner* — Frederick Krass
*Assistant Examiner* — Olga V Tcherkasskaya
(74) *Attorney, Agent, or Firm* — Lerner, David, Littenberg, Krumholz & Mentlik, LLP

(57) ABSTRACT

Disclosed are mascara compositions containing a first acrylates copolymer having a relatively low glass transition temperature (Tg) which is less than about 0° C., a second acrylates copolymer having a relatively high glass transition temperature which is between about 0° C. and less than about 60° C., wherein a mixture of the first and second acrylates copolymers has a Tg less than about 20° C., and a solvent. Also disclosed are methods for making the mascara and applying them to keratinous tissue such as eyelashes in order to enhance their appearance.

10 Claims, No Drawings

MASCARA COMPOSITIONS CONTAINING AT LEAST TWO ACRYLATE FILM FORMERS

CROSS-REFERENCE TO RELATED APPLICATIONS

The present application is a continuation of U.S. patent application Ser. No. 12/456,505, filed on Jun. 17, 2009, which claims the benefit of the filing date of U.S. Provisional Patent Application No. 61/132,448 filed Jun. 18, 2008, the disclosures of which are incorporated herein by reference.

BACKGROUND OF THE INVENTION

U.S. Pat. No. 7,351,418 teaches cosmetic compositions such as mascara that contain a polymer containing a specific heteroatom in a composition comprising particles of a film-forming polymer dispersed in the composition medium, which improves adhesion properties and allows for a thick deposit of the composition on the keratin materials.

U.S. Pat. No. 7,351,405 teaches wax-free mascara compositions containing solid particles of a film-forming acrylic polymer dispersed in a cosmetically acceptable aqueous medium. According to the patent teachings, the compositions are easy to apply, coat the eyelashes well, and after drying form a smooth, uniform deposit and provides a natural makeup result that is comfortable and stays on well over time and that does not wear away, and will remain deposited on eyelashes and/or eyebrows for more than one day or even more than two days.

U.S. Pat. No. 7,094,842 teaches cosmetic compositions, including mascara, that contain at least one aqueous phase containing particles of a substantially linear block silicone copolymer and least one polymer containing at least one monomer having an ethylenic unsaturation and a sulphonic group, and/or at least one organic powder.

SUMMARY OF THE INVENTION

A first aspect of the present invention is directed to a mascara composition, comprising a first acrylates copolymer having a relatively low glass transition temperature (Tg) which is less than about 0° C., a second acrylates copolymer having a relatively high glass transition temperature which is between about 0° C. and less than about 60° C. inclusive, wherein a mixture of said first and second acrylates copolymers has a Tg less than about 20° C., and a solvent. Also disclosed are packages, e.g., blister packages, including a container comprising the mascara composition, and optionally an applicator for applying the composition to eye lashes.

A second aspect of the present invention is directed to a method of preparing a mascara composition, comprising mixing a first acrylates copolymer having a relatively low glass transition temperature which is less than about 0° C., a second acrylates copolymer having a relatively high glass transition temperature which is between about 0° C. and about 60° C. inclusive, and a solvent, wherein a mixture of said first and second acrylates copolymers has a Tg less than about 20° C.

A third aspect of the present invention is directed to a method of making up or enhancing the appearance of eye lashes, comprising applying to eye lashes a mascara composition comprising a first acrylates copolymer having a relatively low glass transition temperature which is less than about 0° C., a second acrylates copolymer having a relatively high glass transition temperature which is between about 0° C. and about 60° C. inclusive, and a solvent, wherein a mixture of said first and second acrylates copolymers has a Tg less than about 20° C.

Underlying the present invention is the discovery that the combination of acrylates copolymers having relatively low and high Tgs provides mascara compositions having improved rheological, texture and wear properties. Mascara compositions of the present invention may be applied to individual eye lashes more evenly, thus providing a relatively smooth, flexible hold and with little clumping or flaking. As illustrated in the working examples herein, an embodiment of the present invention exhibited unexpectedly greater lift or curl and length to eye lashes compared to commercial products that contained only one of the acrylates copolymers.

DETAILED DESCRIPTION

The acrylates copolymers useful in the present invention are more generally referred to in the art as acrylic film-forming dispersions as they are commercially available in the form of liquid dispersions or emulsions. In the mascara compositions of the present invention, a first acrylates copolymer has a relatively low glass transition temperature (Tg). The term "glass transition temperature" generally refers to the temperature at which the amorphous material changes from a glassy solid state to a rubbery state. This temperature may be measured by standard techniques in the art, such as DSC (Differential Scanning calorimetry), e.g., according to the ASTM D3418-97 standard. As used herein, the term "about" allows for imprecision in the use of a particular technique, or the variation between or among various techniques, in determining Tg. Thus, the term provides variability in the order of ±2° C. The term "about X° C." thus includes X° C.

The first acrylates copolymer has a Tg of less than about 0° C. The minimum Tg cannot be so low such that the Tg of a mixture of the first and second acrylates copolymers is less than about 20° C. The minimum Tg of the first acrylates copolymer is typically about −30° C. In some embodiments, the first acrylates copolymer comprises ethyl acrylates/methyl methacrylates copolymer emulsion (chemical name) (INCI name: water (and) acrylates copolymer), which is commercially available from Kobo Products, Inc. (South Plainfield, N.J.) and Daito Kasei Kogyo Co., Ltd., under the trade name Daitosol AD. This product is sold in the form of an emulsion that contains water, ethyl acrylates/methyl methacrylates copolymer, sodium dehydroacetate, and Laureth-20 (lauryl alcohol and oxirane). Daitosol AD is disclosed to have a glass transition temperature of −14° C. See, United States Patent Application Publication 20060134043 A1.

In some embodiments, the first acrylates copolymer comprises ethyl methacrylates/N-butyl acrylates/2-methylhexyl acrylates copolymer emulsion (chemical name) (INCI name: water (and) acrylates/ethylhexyl acrylates copolymer), which is also commercially available from Kobo Products, Inc. and Daito Kasei Kogyo Co., Ltd., under the trade name Daitosol SJ. This product is sold in the form of an emulsion that contains water, ethyl methacrylates/N-butyl acrylates/2-methylhexyl acrylates copolymer, and Laureth-20. Daitosol 5000 SJ is disclosed to have a glass transition temperature of −13° C.

In some other embodiments, the first acrylates copolymer comprises an alkyl(meth)acrylates copolymer emulsion (INCI name: acrylates copolymer), which is commercially available from Nippon LSC Ltd., under the trade name Yodosol GH34F. Yodosol GH34F is disclosed to have a glass transition temperature of −16° C. See U.S. Patent Application Publication 20060134043 A1.

Yet other acrylates copolymers having Tg's less than about 0° C. that may be useful in the present invention include acrylates/ammonium methacrylates copolymer (INCI name) (CAS No. 25212-88-8), commercially available from Ganz Chemical under the tradename ULTRASOL, and which has a Tg of about −20° C. The chemical composition ULTRASOL includes, in addition to the copolymer, water, zinc oxide, sodium lauryl sulfate, and methylparaben.

The second acrylates copolymer has a relatively high glass transition temperature (Tg). The term "relatively high glass transition temperature," as used in the context of the present invention, refers to an acrylates copolymer having a Tg equal to or greater than about 0° C., such as for example a Tg greater than about 0° C. but less than about 60° C.

In some embodiments, the second acrylates copolymer comprises a styrene/acrylates copolymer emulsion (INCI name), which is commercially available from Nippon LSC Ltd., under the tradename Yodosol GH41F. See, U.S. Patent Application Publication 20030074743 A1. Yodosol GH41F is disclosed to have a glass transition temperature of about 5° C.

In other embodiments, the second acrylates copolymer comprises a styrene/acrylates copolymer emulsion (INCI name), and which is commercially available from BASF under the tradename Joncryl 77 (which contains the copolymer in the form of an ammonia salt, along with water and polypropylene glycol). This acrylates copolymer has a Tg of about 35° C.

In yet other embodiments, the second acrylates copolymer comprises a Polyacrylates-21 (and) acrylates/dimethylaminoethyl methacrylates copolymer (INCI name), commercially available from Interpolymer under the tradename Syntran 5100. This acrylates copolymer has a Tg of about 32° C. The chemical composition of Syntran 5100 includes, in addition to water and the two acrylates copolymers having CAS Nos. 68541-61-7 and 67380-24-9 respectively, ethoxylated secondary alcohol (CAS No. 84133-50-6) and sodium laurylpolyethoxyethanol sulfate (CAS No. 68891-38-3).

In yet other embodiments, the second acrylates copolymer comprises a styrene/acrylates/ammonium methacrylates copolymer (and) butylene glycol (and) sodium Laureth-12 sulfate (INCI name), commercially available from Interpolymer under the tradename Syntran 5760 as a 40% aqueous dispersion. This acrylates copolymer has a Tg of about 19° C.

In yet other embodiments, the second acrylates copolymer comprises a polyurethane-10 and PEG-12 dimethicone alcohol copolymer emulsion (INCI name), commercially available from Nippon LSC under the tradename Yodosol PUD (which also includes ethanol, 2-phenoyl-ethanol, and water in the emulsion). This acrylates copolymer has a Tg of about 39° C.

The first acrylates copolymer is present in the inventive compositions in amounts generally ranging from about 5 to about 30%, and in some embodiments from about 8 to about 25%. The second acrylates copolymer is present in the inventive compositions in amounts generally ranging from about 2 to about 20%, and in some embodiments from about 3 to about 15%. These amounts are on a non-dry weight basis. Thus, the combination of the first and second acrylates copolymers is present in the inventive compositions in a total amount of about 10 to about 30% on a non-dry weight basis, based on the total weight of the mascara composition. The first and second acrylates copolymers do not have to be present in equal or even nearly equal amounts in order to achieve the intended Tg.

The mascara compositions of the present invention contain a solvent. The solvent may be polar or non-polar, volatile or non-volatile, or aqueous or non-aqueous in nature. Representative volatile solvents include non-polar volatile hydrocarbon-based oils (which as used herein, refers to oil containing only hydrogen and carbon atoms), silicone oils (optionally comprising alkyl or alkoxy groups that are pendant or at the end of a silicone chain), and fluoro oils. Suitable hydrocarbon-based oils include isoparaffins, i.e., branched alkanes containing 8-16 carbon atoms, such as isododecane (also known as 2,2,4,4,6-pentamethylheptane), and petroleum distillates. Suitable silicone oils may include linear or cyclic silicones containing from 2 to 7 silicon atoms, these silicones optionally comprising alkyl or alkoxy groups containing from 1 to 10 carbon atoms. Examples include octamethylcyclotetrasiloxane, decamethylcyclopentasiloxane, hexadecamethylcyclohexasiloxane, heptamethylhexyltrisiloxane and heptamethyloctyltrisiloxane, and mixtures thereof. Mixtures of these solvents may be used. Polar volatile solvents may also be used, examples of which include $C_2$ to $C_5$ alcohols, such as ethanol, ethyl 3-ethoxypropionate and isohexyl neopentanoate.

The volatile solvent is present in the mascara of the present invention in an amount generally ranging up to about 90%, and in some embodiments, about 5% to about 80%, and in other embodiments, from about 10% to about 70%, based on the total weight of the mascara.

Exemplary non-polar non-volatile solvents include polyalphaolefins, which include ethylene derivatives oligomerized into even-numbered carbon polyalphaolefins e.g., $C_6$-$C_{14}$ olefins such as polydecene and polymers of $C_6$, $C_8$, $C_{12}$ and C14 olefins. The polyolefins may have a molecular weight (MW) generally ranging from about 280 to about 11,500, and a viscosity (CPs at about 20° C.) generally ranging from about 7 to about 32,500. They may also be hydrogenated. In some embodiments, the non-volatile solvent includes PureSyn™ 2 (MW about 283), 4 (MW about 432), 6 (MW about 570), 8 (MW about 611), 150 (MW about 3980) and 300 (MW about 4870) (INCI name: hydrogenated polydecene). The viscosity of these polymers is about 8, about 33, about 64, about 103, about 4179 and about 8400, respectively.) PureSyn™ 100 (MW about 2939, viscosity about 3900, INCI name: hydrogenated $C_{6-14}$ olefin polymers) and PureSyn™ 1000 (MW about 11,500, viscosity about 32,400, INCI name: polydecene) may also be useful. The PureSyn™ products are available from Exxon Chemicals.

The non-volatile solvent is present in the mascara of the present invention in an amount generally ranging from about 0.1% to about 70%, and in some embodiments, about 0.5% to about 40%, and in other embodiments, 1% to about 25%, based on the total weight of the mascara.

The inventive compositions may contain any other cosmetically or dermatologically acceptable and, in general, physiologically acceptable oil, such as carbon-based, hydrocarbon-based, fluoro and/or silicone oils, of mineral, animal, plant or synthetic origin, alone or as a mixture. These ingredients, along with any non-polar solvents, would constitute a liquid fatty phase of the mascara composition.

The solvent may or may not include water. Mascara that is washable contains water. On the other hand, water may or may not be present in waterproof mascara. Generally, water content of washable mascaras ranges from about 20 to about 80% by weight, and in some embodiments from about 30 to about 60% by weight of the mascara composition. In contrast, water content of waterproof mascaras generally ranges from about 0 to about 60% by weight, and in some embodiments from about 0 to about 35% by weight of the mascara composition. One or more water-miscible solvents (miscibility in water of greater than 50% by weight at about 25° C.) may also be present. Examples include lower monoalcohols containing from 1 to 5 carbon atoms such as ethanol and isopropanol, glycols containing from 2 to 8 carbon atoms, such as propylene glycol, ethylene glycol, butylene glycol or dipropylene glycol and pentylene glycol, $C_3$-$C_4$ ketones and $C_2$-$C_4$ aldehydes.

In those embodiments wherein the mascara composition contains water, the compositions of the invention also contain an emulsifier. Emulsifiers typically employed in the compositions of the present invention include anionic, nonionic and cationic emulsifiers. See, e.g., Encyclopedia of Chemical Technology, KIRK-OTHMER, volume 22, pp. 333-432, 3rd edition, 1979, Wiley, for the definition of the properties and (emulsifying) functions of the emulsifiers, in particular pp. 347-377 of this publication regarding anionic and nonionic emulsifiers. Examples of emulsifiers useful in the compositions of the invention include as nonionic emulsifiers, fatty acids, fatty alcohols, polyethoxylated fatty alcohols or polyglycerolated fatty alcohols, such as polyethoxylated stearyl alcohols or cetylstearyl alcohols, esters of fatty acid and sucrose, and glucose alkyl esters, in particular polyoxyethylenated $C_1$-$C_6$ alkyl glucose fatty esters, and as anionic emulsifiers, $C_{16}$-$C_{30}$ fatty acids neutralized by amines, ammonia or the alkali metal salts thereof. Examples of cationic emulsifiers include quaternary amines, amine oxides and amines, e.g., alkyl amines, alkyl imidazolines, ethoxylated amines, quaternary compounds, and quaternized esters. Cationic emulsifiers may also provide a conditioning effect.

Emulsifiers are generally present in amounts ranging from about 1 to about 30% by weight, and in some other embodiments from about 3% to about 15% by weight, relative to the total weight of the composition.

The compositions of the present invention may further contain at least one further (e.g., cosmetically or dermatologically acceptable) ingredient, including additives and adjuvants, including, for example, waxes, polymers, thickeners, moisturizers, anti-foam agents (e.g., simethicone, which is a fluid composition containing polydimethylsiloxane and silica), colorants, dispersion enhancing agents, fillers (e.g., powders and Mothers of pearl), fibers, sunscreen agents, preservatives, chelators (such as EDTA and salts thereof, particularly sodium and potassium salts), antioxidants (e.g., BHT, tocopherol), essential oils, fragrances, neutralizing or pH-adjusting agents (e.g., sodium hydroxide), and cosmetically active agents and dermatological active agents such as, for example, anti-inflammatory agents, defoaming agents, emollients, vitamins, trace elements and essential fatty acids. These ingredients may be soluble or dispersible in whatever phase or phases are present in the mascara (i.e., aqueous and/or fatty phase).

In view of the presence of the two acrylates copolymers, waxes are optional. Some embodiments of the present invention are therefore wax-free. For the purposes of the present invention, the term "wax" means a lipophilic fatty compound that is solid at room temperature about (25° C.) and atmospheric pressure (760 mmHg, i.e., 105 Pa), which undergoes a reversible solid/liquid change of state and which has a melting point of greater than 30° C. and in some embodiments, greater than about 55° C. up to about 120° C. or even as high as about 200° C. For the purposes of the invention, the waxes are those generally used in cosmetics and dermatology. A variety of waxes may be useful, including waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fibre waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes. Alternatively, hydrogenated oils of animal or plant origin may be used. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils. In some embodiments, the compositions contain at least two or at least three waxes. The wax may be present in the compositions in an amount generally ranging from about 0.1% to about 40%, and in some embodiments from about 0.5% to about 20%, or from about 1% to about 10% by weight, relative to the total weight of the composition.

The combination of the two acrylates copolymers also renders optional the inclusion of additional film formers such as polymers. Nonetheless, the mascara compositions may contain other polymers, e.g., film forming polymers, provided that they are compatible with the other ingredients in the inventive compositions, particularly the acrylates copolymers. The polymer may be present in the compositions in an amount generally ranging from 0 to about 20% by weight.

Viscosity may be adjusted by adding an oil phase thickener or an agent useful for gelling a liquid fatty phase. Gelling agents may be chosen from gelling agents in polymeric form and gelling agents in mineral form. The gelling agent may be selected from the group consisting of agents that gel via chemical reticulation and agents that gel via physical reticulation. Modified clays may be used as gelling agents, examples of which include hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearalkonium bentonites, such as the products sold or made under the names Claytone APA and Claytone AF by the company Southern Clay, and Baragel 24 sold or made by the company Rheox. Other mineral gelling agents include silica, such as fumed silica. The fumed silica may have a particle size ranging from about 5 nm to 200 nm.

Water-soluble thickeners or gelling agents that may be used include polyvinylpyrrolidone (PVP), polyvinyl alcohol, crosslinked acrylates (e.g. Carbopol 982), hydrophobically-modified acrylates (e.g. Carbopol 1382); polyacrylamides such as, for example, the crosslinked copolymers sold under the names Sepigel 305 (CTFA name: polyacrylamide/C13-C14 isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulphonic acid polymers and copolymers, that are optionally crosslinked and/or neutralized; cellulose derivatives such as hydroxyethylcellulose, sodium carboxymethylcellulose, hydroxypropyl methylcellulose, hydroxypropyl cellulose, ethyl cellulose and hydroxymethyl cellulose; polysaccharides and gums, e.g., natural gums such as xanthan gum, sclerotium, carrageenan and pectin; polysaccharide resins such as starch and its derivatives, hyaluronic acid and its salts, clays, and, in particular, montmorillonites, hectorites, bentonites, and laponites, crosslinked polyacrylic acids, such as the "Carbopol" products from the company Goodrich, the polyglyceryl(meth)acrylates polymers sold under the names "Hispagel" or "Lubragel" by the companies Hispano Quimica or Guardian, crosslinked acrylamide polymers and copolymers, such as those sold under the names "PAS 5161" or "Bozepol C" by the company Hoechst, "Sepigel 305" by the company SEPPIC, crosslinked methacryloyloxyethyltrimethylammonium chloride homopolymers sold under the name "Salcare SC95" by the company Allied Colloid, and associative polymers and, in particular associative polyurethanes.

Compositions of the present invention may also contain a moisturizer. Examples include sodium lactate, mannitol, amino acids, hyaluronic acid, lanolin, urea, petroleum jelly and mixtures thereof. Other examples include polyols such as glycerin, diglycerin, triglycerin, polyglycerin, polyethylene glycol, ethylene glycol, diethylene glycol, triethylene glycol, propylene glycol, dipropylene glycol, hexylene glycol, 1,3-butylene glycol, 1,4-butylene glycol and sorbitol. These agents may be present in the compositions of the present invention in amounts generally ranging from about 0.1% to about 20%, and in some embodiments, from about 0.5% to about 15% by weight of the composition.

Colorants may be chosen from the lipophilic dyes, hydrophilic dyes, traditional pigments, and nacres usually used in cosmetic or dermatological compositions, and mixtures thereof. The coloring agent may have any shape, such as, for example, spheroidal, oval, platelet, irregular, and mixtures thereof. Pigments may optionally be surface-treated e.g., with silicones (e.g., inorganic pigments may be coated with simethicone), perfluorinated compounds, lecithin, and amino acids.

The liposoluble dyes include, for example, Sudan Red, D&C Red 17, D&C Green 6, soybean oil, Sudan Brown, D&C Yellow 11, D&C Violet 2, D&C Orange 5, quinoline yellow and annatto. The water-soluble dyes are, for example, beetroot juice or methylene blue.

The pigments may be chosen from white pigments, colored pigments, inorganic pigments, organic pigments, coated pigments, uncoated pigments, pigments having a micron size and pigments not having a micron size. Among the inorganic pigments that may be mentioned are titanium dioxide, optionally surface-treated, zirconium oxide, zinc oxide, cerium oxide, chromium oxide, manganese violet, ultramarine blue, chromium hydrate, and ferric blue. Among the organic pigments which may be mentioned are carbon black, pigments of D&C type, lakes based on cochineal carmine, lakes based on barium, lakes based on strontium, lakes based on calcium, and lakes based on aluminum.

The nacreous pigments may, for example, be chosen from white nacreous pigments such as mica coated with titanium and mica coated with bismuth oxychloride, colored nacreous pigments such as titanium mica with iron oxides, titanium mica with, for example, ferric blue and/or chromium oxide, titanium mica with an organic pigment of the type mentioned above, as well as nacreous pigments based on bismuth oxychloride, interferential pigments, and goniochromatic pigments.

Colorants are generally present in an amount ranging from about 0.01% to about 50% relative to the total weight of the composition.

The compositions of the present invention may also contain dispersion enhancing agents such as polysaccharide resins, e.g., KM 13, available from KAMA International Corp. (Duluth, Ga.). Dispersion enhancing agents are especially preferred in pigmented products.

Fillers, powders and mothers-of-pearl may also be present, typically to modify the texture of the composition and the matteness/gloss effect. Fillers should be understood to mean lamellar or non-lamellar, inorganic or synthetic, colorless or white particles. Mothers-of-pearl should be understood to mean iridescent particles produced especially by certain mollusks in their shell or else synthesized. Representative examples of these ingredients include mica, silica, kaolin, iron oxides, titanium dioxide, polyamide powders, polyamide powders, for instance Nylon® (Orgasol from Atochem), poly-alanine powders, polyethylene powders, tetrafluoroethylene polymer powders, for instance Teflon®, starch, boron nitride, hollow polymer microspheres such as those of polyvinylidene chloride/acrylonitrile, for instance Expancel® (Nobel Industrie), acrylic powders such as Polytrap® (Dow Corning), polymethyl methacrylates particles and silicone resin microbeads (for example Tospearls® from Toshiba), magnesium hydrocarbonate, hydroxyapatite, hollow silica microspheres (Silica Beads® from Maprecos), and glass and ceramic microcapsules. Filler(s), if present, are in amounts generally ranging from about 0.1% to about 25%, and in some embodiments from about 1% to about 20% by weight of the total weight of the composition.

In some embodiments, the mascara may further contain fibers to allow an improvement in the lengthening effect. The fibers useful in the present invention may be chosen from natural and synthetic fibers. Natural fibers include, but are not limited to, cotton, silk, wool, and other keratin fibers. Synthetic fibers include, but are not limited to, polyester, rayon, nylon and other polyamide fibers. The fibers may be present in the compositions in an amount generally ranging from about 0.01% to about 10% by weight of the composition.

Representative examples of preservatives include alkyl para-hydroxybenzoates, wherein the alkyl radical has from 1, 2, 3, 4, 5 or 6 carbon atoms and preferably from 1 to 4 carbon atoms e.g., methyl para-hydroxybenzoate(methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben), and phenoxyethanol. Mixtures of preservatives are also useful, e.g., the mixture of methylparaben, ethylparaben, propylparaben and butylparaben sold under the name Nipastat by Nipa, the mixture of phenoxyethanol, methylparaben, ethylparaben, propylparaben and butylparaben, also sold by Nipa under the name Phenonip, and the mixture of phenoxyethanol, methylparaben, isopropylparaben, isobutylparaben and butylparaben, sold by ISP under the tradename Liquapar Optima. The preservative may be present in an amount generally ranging from about 0.01% to about 15% by weight of the composition.

The following examples are intended to further illustrate the present invention. They are not intended to limit the invention in any way. Unless otherwise indicated, all parts are by weight.

EXAMPLES

Example 1

A mascara composition of the present invention is described below.

| PHASE | INGREDIENTS | AMOUNT (Wgt %) |
|---|---|---|
| A1 | Water | 44.66 |
|  | Methylparaben | 0.17 |
|  | Liquapar Optima | 1.2 |
|  | Disodium EDTA | 0.20 |
|  | Sodium Dehydroacetate | 0.20 |
|  | Butylene Glycol | 3.90 |
|  | Simethicone | 0.10 |
|  | PEG-200 Glyceryl Stearate | 4.00 |
| A2 | Sunpuro (iron oxide pigment) | 7 |
| A3 | Simulgel 600 | 3.50 |
| B1 | Beeswax | 7.40 |
|  | Carnauba Wax | 3.50 |
|  | Propylparaben | 0.02 |
|  | Ethylparaben | 0.15 |
| C | Yodosol GH41F | 12 |
|  | Yodosol GH34F | 8 |
| D | Alcohol | 3 |
| E | Rayon Fibers | 1 |
|  |  | 100.00 |

The mascara composition described above was prepared as follows. The water was added to a main beaker, followed by initiating of heating at about 85-90° C. using a homogenizer. Methylparaben was added, with mixing until dissolved. The remaining ingredients in Phase A1, i.e., Liquapar Optima, disodium EDTA, sodium dehydroacetate, butylene glycol, Simethicone, and the PEG-200 glyceryl stearate, were added individually with mixing for 5 minutes for each added ingredient. Once all the Phase A1 ingredients were dissolved, the Phase A2 ingredient was added, and dispersed for one hour using the homogenizer, while keeping the temperature at about 85° C. The Phase A3 ingredient, i.e., Simulgel 600, was slowly added under conditions of high shear for 30 minutes. In another beaker, the Phase B1 ingredients were added together at a temperature of about 85-90° C., in order to melt the beeswax and carnauba wax. The ingredients in the side beaker were then added to the main beaker and then emulsified for about 20 minutes. The resultant emulsified mixture was changed to a Lightning mixer using a paddle blade, followed by initiation of cooling to about 40° C., followed by addition of the Phase C ingredients, i.e., the two acrylates copolymers. The Phase D ingredient, i.e., alcohol, was added at a temperature of about 25-28° C., followed by the addition of the Phase E ingredient, i.e., the rayon fibers.

Example 2

The inventive mascara composition was compared to two of the assignee's commercial mascara compositions, which differ from the inventive composition mainly in that they contain only one of the two acrylates copolymers. The comparisons were from the standpoints of lift (or curl) and length. The results showed that the inventive composition containing the combination of the low Tg and the high Tg acrylates copolymers provided a statistically significant (as confirmed by One Way Repeated Measures ANOVA with $p \leq 0.05$), maintained lift after eight (8) hours.

All publications cited in the specification, both patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A mascara composition, comprising a first acrylates film-forming copolymer, a second acrylates film-forming copolymer, and a solvent, wherein a mixture of said first and second acrylates copolymers has a glass transition temperature (Tg) less than about 20° C., wherein the first acrylates film forming copolymer comprises acrylates copolymer and has a glass transition temperature of about −16° C., and wherein said second acrylates film forming copolymer comprises styrene/acrylates copolymer and has a glass transition temperature of about 5° C., and wherein said first film forming acrylates copolymer and said second acrylates film forming copolymer are present in the mascara composition in a weight ratio of about 1:1.5, and wherein the first acrylates film forming copolymer is present in an amount of from about 5% to about 30% on a non-dry weight basis, and the second acrylates film forming polymer is present in an amount of about 2% to about 20% on a non-dry weight basis, each based on the total weight of the mascara composition.

2. The mascara composition of claim 1, wherein said solvent comprises water, and wherein said composition further comprises an emulsifier.

3. The mascara composition of claim 1, wherein said solvent comprises a non-aqueous solvent.

4. The mascara composition of claim 3, wherein said non-aqueous solvent comprises isododecane or petroleum distillate.

5. The mascara composition of claim 1, further comprising a colorant.

6. The mascara composition of claim 1, further comprising fibers.

7. The mascara composition of claim 1, further comprising a wax.

8. A package, comprising a container having disposed therein the mascara of claim 1, and optionally an applicator for applying the mascara composition to eye lashes.

9. A method of preparing a mascara composition, comprising mixing together a first acrylates film-forming copolymer, a second acrylates film-forming copolymer, and a solvent, wherein a mixture of said first and second acrylates film-forming copolymers has a Tg less than about 20° C., wherein the first acrylates film forming copolymer comprises acrylates copolymer and has a glass transition temperature of about −16° C., and wherein said second acrylates film forming copolymer comprises styrene/acrylates copolymer and has a glass transition temperature of about 5° C., and wherein said first acrylates film forming copolymer and said second acrylates film forming copolymer are present in the mascara composition in a weight ratio of about 1:1.5, and wherein the first acrylates film forming copolymer is present in an amount of from about 5% to about 30% on a non-dry weight basis, and the second acrylates film forming polymer is present in an amount of about 2% to about 20% on a non-dry weight basis, each based on the total weight of the mascara composition.

10. A method of making up or enhancing the appearance of eye lashes, comprising applying to eye lashes a mascara composition comprising a first acrylates film-forming copolymer, a second acrylates film forming copolymer, and a solvent, wherein a mixture of said first and second acrylates film-forming copolymers has a Tg less than about 20° C., wherein the first acrylates film forming copolymer comprises acrylates copolymer and has a glass transition temperature of about −16° C., and wherein said second acrylates film forming copolymer comprises styrene/acrylates copolymer and has a glass transition temperature of about 5° C., and wherein said first acrylates film forming copolymer and said second acrylates film forming copolymer are present in the mascara composition in a weight ratio of about 1:1.5, and wherein the first acrylates film forming copolymer is present in an amount of from about 5% to about 30% on a non-dry weight basis, and the second acrylates film forming polymer is present in an amount of about 2% to about 20% on a non-dry weight basis, each based on the total weight of the mascara composition.

\* \* \* \* \*